United States Patent
Tatsumi (10) Patent No.: US 10,610,372 B2
(45) Date of Patent: Apr. 7, 2020

(54) VERTEBRAL FIXATION PLATE SYSTEM AND METHOD FOR USE

(71) Applicant: RLT Healthcare, LLC, Lake Oswego, OR (US)

(72) Inventor: Robert L. Tatsumi, Lake Oswego, OR (US)

(73) Assignee: RLT Healthcare, LLC, Lake Oswego, OR (US)

( * ) Notice: Subject to any disclaimer, the term of this patent is extended or adjusted under 35 U.S.C. 154(b) by 572 days.

(21) Appl. No.: 15/093,494

(22) Filed: Apr. 7, 2016

(65) Prior Publication Data

US 2016/0296341 A1    Oct. 13, 2016

Related U.S. Application Data

(60) Provisional application No. 62/153,419, filed on Apr. 27, 2015, provisional application No. 62/144,225, filed on Apr. 7, 2015.

(51) Int. Cl.
*A61F 2/44* (2006.01)
*A61F 2/30* (2006.01)

(52) U.S. Cl.
CPC .......... *A61F 2/4455* (2013.01); *A61F 2/447* (2013.01); *A61F 2002/3054* (2013.01); *A61F 2002/3093* (2013.01); *A61F 2002/30187* (2013.01); *A61F 2002/30331* (2013.01); *A61F 2002/30354* (2013.01); *A61F 2002/30367* (2013.01); *A61F 2002/30373* (2013.01); *A61F 2002/30433* (2013.01); *A61F 2002/30494* (2013.01); *A61F 2002/30553* (2013.01); *A61F 2002/30578* (2013.01); *A61F 2002/4475* (2013.01); *A61F 2220/0041* (2013.01)

(58) Field of Classification Search
CPC ............ A61F 2/4455; A61F 2002/4435; A61F 2/447; A61F 2002/4475; A61F 2220/0041; A61B 17/8004; A61B 17/8009
See application file for complete search history.

(56) References Cited

U.S. PATENT DOCUMENTS

| | | | |
|---|---|---|---|
| 2007/0185489 A1* | 8/2007 | Abdou | A61B 17/7059 606/255 |
| 2007/0270965 A1* | 11/2007 | Ferguson | A61B 17/7059 623/17.11 |
| 2012/0041559 A1* | 2/2012 | Melkent | A61F 2/4455 623/17.11 |

(Continued)

*Primary Examiner* — Matthew J Lawson
(74) *Attorney, Agent, or Firm* — Chernoff, Vilhauer, McClung & Stenzel, LLP (57) ABSTRACT

A vertebral fixation plate system and a method for its use in a surgical procedure to fuse adjacent spinal vertebrae to each other. A base member is fastened to a spinal interbody fusion device installed in place of an injured spinal disc. The base member is received within a receptacle defined in the vertebral fixation plate and mates with the plate, in a selected one of a plurality of available positions of the plate with respect to the base member, and thus with respect to the adjacent vertebrae between which the spinal interbody fusion device is installed. A locator member defined on the base member or the plate is mated in a locating cavity defined in the other one of the base member or the plate to keep the plate in the selected position.

11 Claims, 8 Drawing Sheets

(56) References Cited

U.S. PATENT DOCUMENTS

| | | | |
|---|---|---|---|
| 2012/0185048 A1* | 7/2012 | Phelps | A61F 2/4455 623/17.16 |
| 2014/0107650 A1* | 4/2014 | Dacosta | A61B 17/8009 606/70 |
| 2015/0320569 A1* | 11/2015 | Pisharodi | A61F 2/447 623/17.12 |
| 2016/0367379 A1* | 12/2016 | Refai | A61F 2/447 |

* cited by examiner

VERTEBRAL FIXATION PLATE SYSTEM AND METHOD FOR USE

BACKGROUND OF THE INVENTION

The present invention relates to spine surgery and in particular relates to a vertebral fixation plate system and a method for its implantation and use in fusing vertebrae to one another.

It has long been known that one way to alleviate pain in patients who have suffered degeneration of spinal discs, so-called ruptured discs, is to remove the failed disc and replace it with an intervertebral support which can form a support for bone growth to fuse together the adjacent vertebrae. The conventional procedure for fusion of adjacent vertebrae involves insertion of a bone graft or an interbody fusion device between the vertebrae, together with implantation of a supporting plate by screwing the plate to each of the involved vertebrae to immobilize the vertebrae with respect to each other while the bones become fused together.

Until recently, it has not been considered too important a factor that there is a significant amount of x-ray exposure involved in the way spinal fusion has been performed. Recently, however, the importance of minimizing x-ray exposure, both for a patient and for medical personnel involved in such procedures, has been better appreciated. It is also an important objective in performing spinal fusion procedures to minimize the invasiveness and resulting trauma to the patient from the surgery itself, both by use of smaller incisions and by reducing the amount of time required to perform a procedure properly.

Conventional practice in implantation of vertebral fixation plates, at least in cervical spine fusion procedures, has been to expose the defective cervical disc to be removed, replace it with a bone graft or other interbody fusion device, place a vertebral fixation plate across the space between the vertebrae that are to be fused, in a position selected by the surgeon, and then, in some cases, secure the plate by installation of temporary fixation pins. Typically, a radiographic image is obtained to determine whether the plate is in a satisfactory location, and, if necessary, the location of the plate may be adjusted, but it is desired to minimize the amount of radiation to which a patient and attending physicians are exposed, and so if an image shows the plate not to be located precisely where desired, adjustment may be made without subsequent x-ray images being taken to evaluate the adjustment before the plate is permanently fastened to the involved vertebrae. The plate is then secured to the vertebrae utilizing suitable screws, but there is no common way except for experience to quickly establish an initial optimum position for the vertebral fixation plate.

To fasten the plate to the involved vertebrae, the surgeon may manually hold the plate in the finally determined position while using a drill guide and drill to bore and tap holes in the vertebrae to receive screws to fasten the plate. Alternatively, self-tapping screws may be used once a bore has been made, or self-drilling screws may be utilized, but the position of the plate on the vertebrae, once chosen, is typically maintained manually by the surgeon, with the possible use of temporary fixation pins.

As a result, plates are often implanted in serviceable but less than optimal positions on patients' spinal vertebrae. Thereafter, when a medical care provider studies an x-ray photograph of the affected portion of the patient's spine, if the plate is not aligned completely parallel with the spine, or is located off-center, there may be some serious concern, even if the less-than-perfect location of the plate is completely inconsequential as to its function in securing the vertebrae as they heal in a fused manner.

What is desired, then, is a spinal fixation plate system and a manner of installing it so as to enable a surgeon to perform a spinal fusion procedure in a minimally invasive manner, in a minimum amount of time, and yet to place the plate in the optimum location with respect to the vertebrae being fused.

SUMMARY OF THE INVENTION

An implantable plate system for use in a procedure of fusing vertebrae in a patient is disclosed, along with a method for use thereof. In an implantable plate system disclosed herein, as a principal aspect, an intervertebral graft body may have an attached reference member that may be called a base plate, a base disc, or a base member. A screw can attach the base to the graft body while the plate is fastened to the vertebrae. An inner face of a vertebral fixation plate implant may define a recessed receptacle for the base member. The vertebral fixation plate thus fits closely against the base member with a limited amount of freedom to move with respect to the base member, once the graft body has been installed between the vertebrae to be fused but before the vertebral fixation plate is fastened to the vertebrae.

As one important aspect of the plate system disclosed herein, interactive mating aspects of both the base and the plate can hold the plate in a selected one of several slightly different positions with respect to the base. Thus, the surgeon can install the graft body between vertebrae that are to be fused, and can then, if necessary, attach the base to the graft body, and thereafter place the fixation plate in position bridging the gap between the adjacent vertebrae in what appears to be an optimum location for the plate. The mating portions of the plate and the base will keep the plate in the selected location while that location is radiographically checked. If the radiographic image indicates that adjustment is necessary, the plate may then be moved to a better one of the positions available with respect to the base and retained in that adjusted position by the mating portions of the plate and the base while the plate is fastened to the vertebrae.

As one aspect of the system, a graft body may be manufactured with an integral base member so that it is unnecessary to install the base onto the graft body before the fixation plate is put into place.

In one embodiment of the system disclosed herein, the vertebral fixation plate defines an opening through which a portion of the base member and indicia on the base member may be seen.

As one aspect of the system disclosed herein, there may be a receptacle such as a bore defined in the base member to accept a retainer such as a screw extending into the graft body.

In one embodiment of the system, the base may include one or more projecting locators of a selected shape and size, and corresponding cavities may be provided in the receptacle portion of the fixation plate to receive the locators and hold the plate in a chosen one of several positions with respect to the base. Alternatively, the projecting locators may be present within the recessed receptacle in the inner face of the fixation plate, and corresponding cavities or indentations may be provided in the outer face of the base.

In one embodiment of the system, the several available positions in which the plate may be mated with the base may vary from one another with respect to an angle of rotation of the plate in a plane parallel with a central axis of the portion of the spine including the vertebrae being fused to each other.

In one embodiment of the system, the several available positions in which the plate may be mated with the base may vary from one another in terms of translation of the plate in a lateral or longitudinal direction with respect to the patient's spine.

In one embodiment of the system, an outer face of the vertebral fixation plate aligned with the receptacle for the base may include indicia visible to the surgeon when installing the plate. The position of the plate relative to the base may thus be easily discerned visually and the amount of adjustment of the position of the fixation plate relative to the base member may be seen and verified.

A method for a spinal fusion procedure which is another aspect of the invention disclosed herein includes providing a base member attached to an intervertebral graft body; installing the graft body between a pair of vertebrae to be fused to one another; providing a vertebral fixation plate including a recessed receptacle for matingly receiving the base member; placing the fixation plate in a position spanning a space between the vertebrae to be fused together, with the base member received in the recessed receptacle in a selected one of a plurality of available relative positions; determining whether the fixation plate is in an optimum position with respect to the vertebrae to be fused together; moving the fixation plate, if necessary, to another one of the plurality of available positions relative to the base member; holding the fixation plate stationary with respect to the baseplate; and installing fasteners to secure the fixation plate to the vertebrae to be fused, thereby immobilizing the vertebrae with respect to each other.

According to one embodiment of the method, the base member may be provided as an integral part of the intervertebral graft body, making it unnecessary to install and attach the base member to the graft body after the graft body has been placed between the vertebrae to be fused.

The foregoing and other objectives and features of the apparatus and method disclosed herein will be more readily understood upon consideration of the following detailed disclosure taken in conjunction with the accompanying drawings.

DETAILED DESCRIPTION OF PREFERRED EMBODIMENTS

Figure 1:
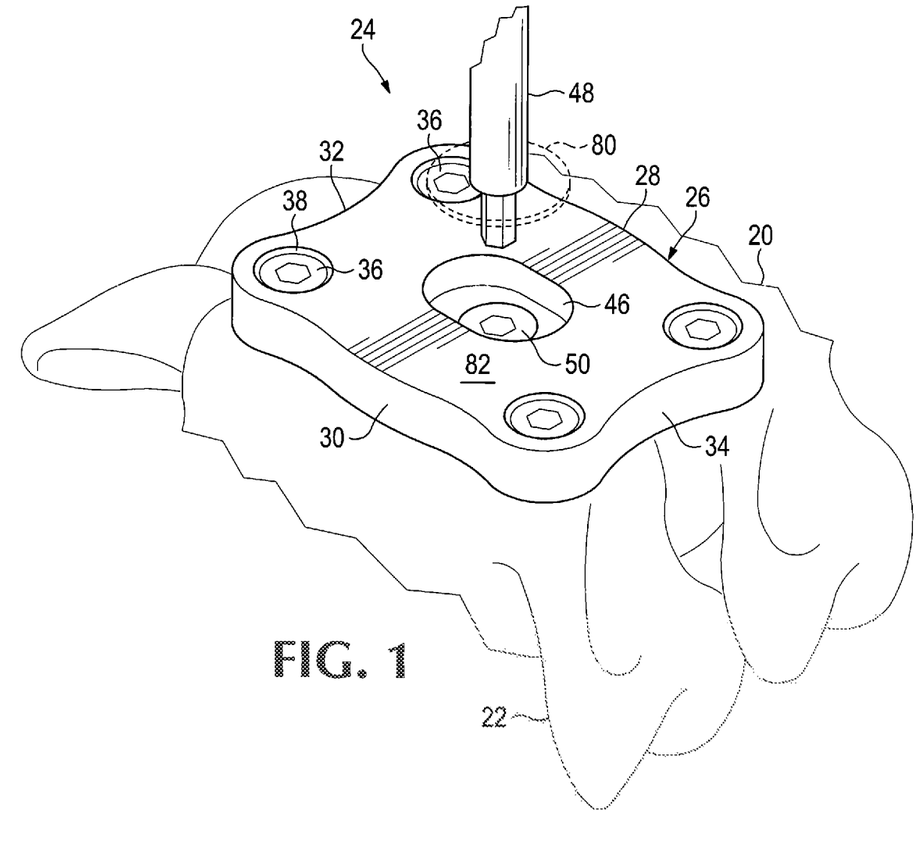
FIG. 1 is an isometric view of two cervical vertebrae of a person's spine, showing a vertebral fixation plate installed according to the present invention as part of a spinal fusion procedure.
Figure 2:
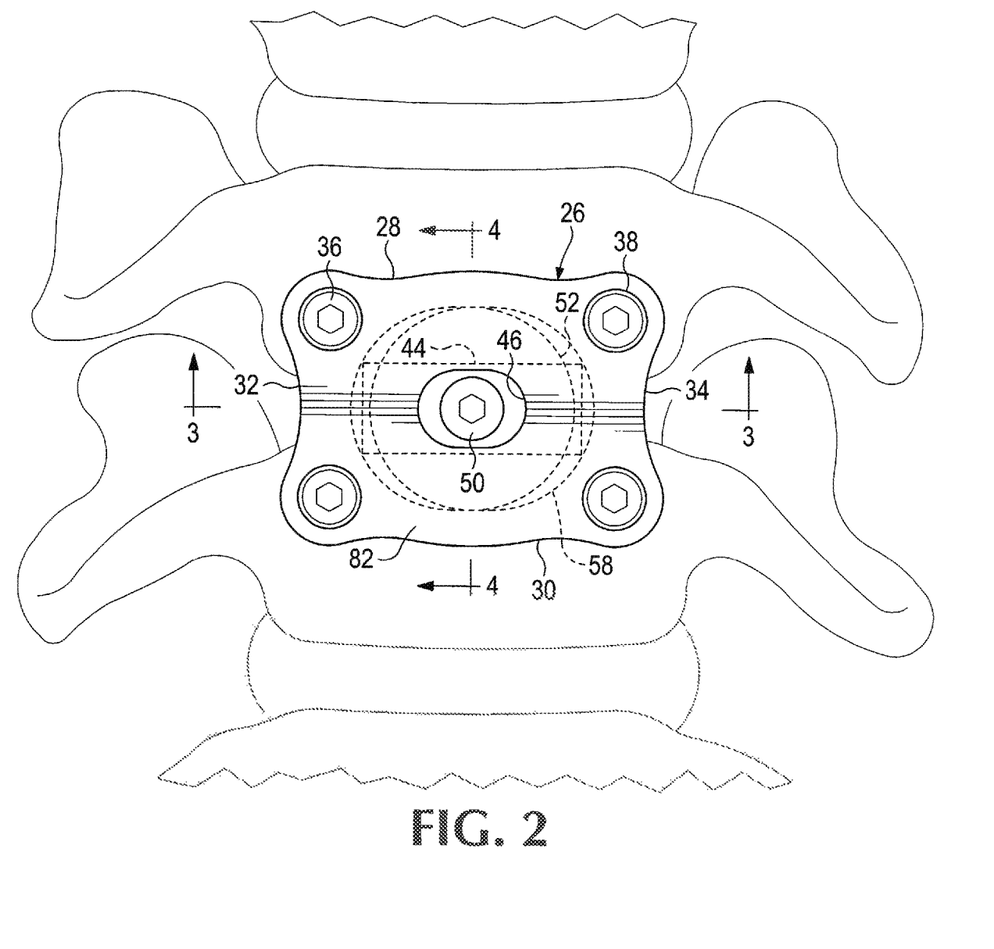
FIG. 2 is a plan view of the portion of a cervical spine shown in FIG. 1, showing the installed vertebral fixation plate.

Referring now to the drawings that form part of the disclosure herein, in FIGS. 1 and 2 a cervical portion of a spine including two adjacent vertebrae 20, 22 is shown with a vertebral fixation plate system 24 in place immobilizing the two vertebrae 20, 22 with respect to each other. A vertebral fixation plate 26 has a pair of opposite ends 28, 30, respectively facing in cephalad and caudal directions, and a pair of opposite lateral sides 32, 34. Fasteners such as screws 36 are mounted in respective receptacles 38 in the corners of the fixation plate 26, from which they extend through respective holes 40 in the fixation plate 26 into each of the vertebrae, as may be seen in FIGS. 3 and 4, a respective pair of the screws connecting each of the opposite ends of the vertebral fixation plate to one of the vertebrae. Ideally, each of the ends, 28, 30 extends a short distance along the respective vertebra to which it is fastened, in order to leave room for an adjacent fixation plate (not shown) should a fusion be desired at the adjacent level of the spine at a later date.

Each of the receptacles 38 may be bowl-shaped, or approximately hemispherical, and the respective hole 40 associated with each receptacle 38 may be larger than the shaft of the screw 36 extending through the hole, so that the screw 36 may be oriented either perpendicular to the fixation plate 26 or at an angle α within a range of a few degrees from being perpendicular to the fixation plate 26. This can simplify installation of the screws 36 and allow each of the screws to be placed into a vertebra at a selected angle α intended to provide a secure attachment of the plate 26 to the vertebra concerned and to provide improved security by virtue of the screws 36 not being parallel with each other.

As with conventional vertebral fixation plates, the screws 36 used may be of any one of several different types, including screws for which bores must be tapped after being made, self-tapping screws, or self-drilling screws, at the election of the surgeon carrying out the spinal fusion procedure utilizing the vertebral fixation plate system 24 disclosed herein.

The vertebral fixation plate 26 bridges the space 42 from which the natural intervertebral disc has been removed from between the pair of adjacent vertebrae 20, 22 and where an interbody fusion device 44, hereinafter called a graft body, has been installed. In FIGS. 1-5, it may be seen that the vertebral fixation plate 26 defines a central opening 46 aligned with the graft body 44, and a tool 48 is shown aligned with, but spaced apart from a tool socket in the head of a fastener 50, which may be a screw, visible through the opening.

Figure 3:
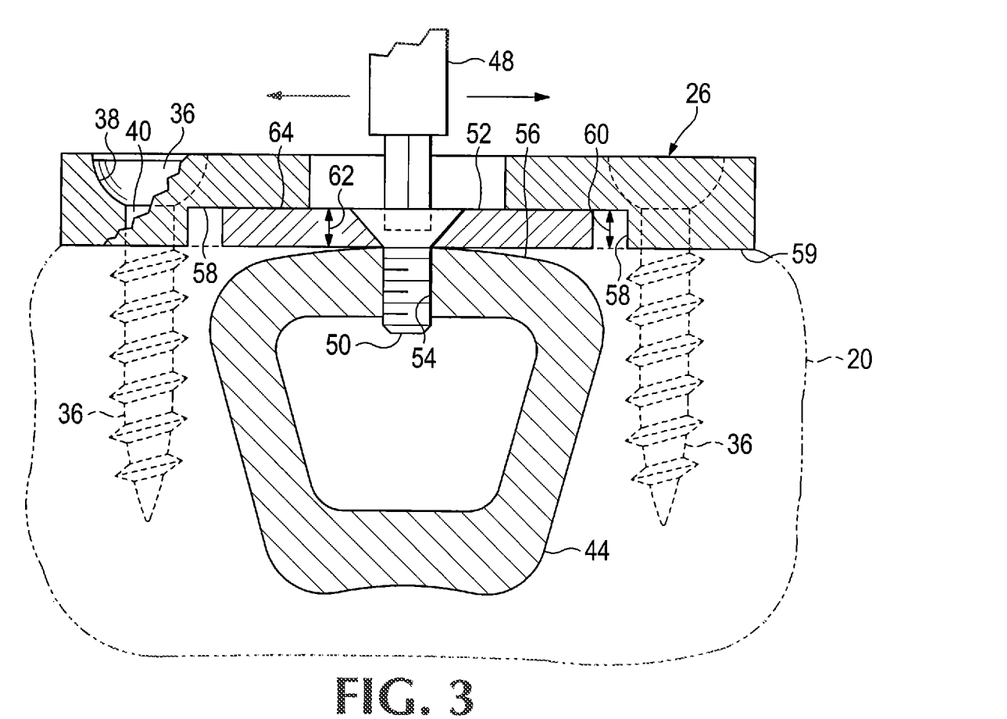
FIG. 3 is a sectional view taken along line 3-3 of FIG. 2.
Figure 4:
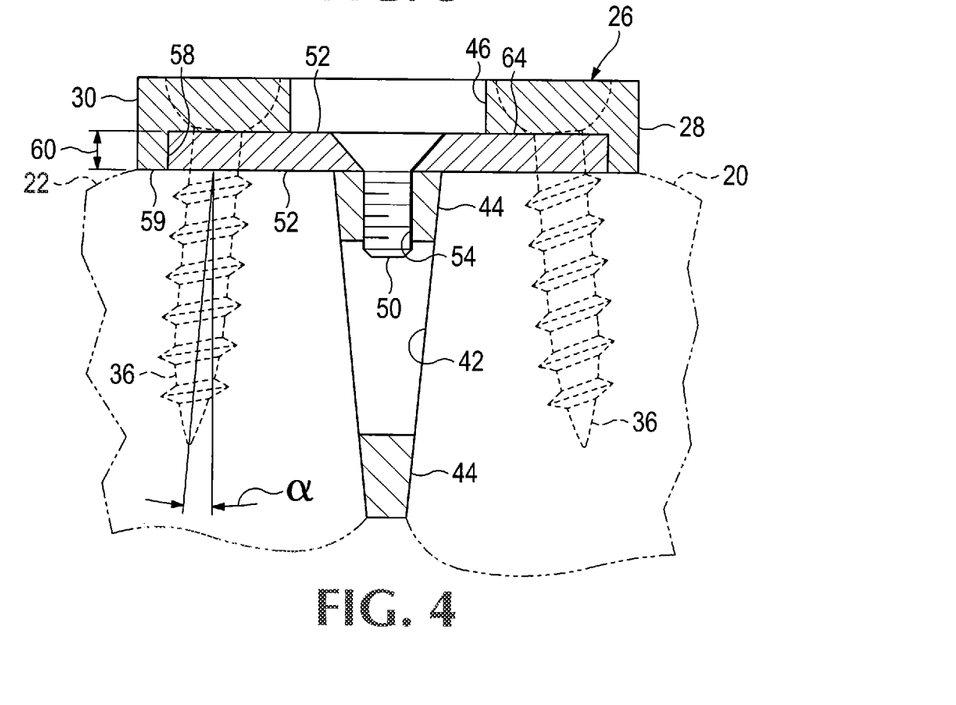
FIG. 4 is a sectional view taken along line 4-4 of FIG. 2.

As shown in FIGS. 3 and 4, the screw 50 visible in FIG. 1 is countersunk in a base member 52 and extends through the base member into a central bore 54 in an adjacent front face 56 of the intervertebral graft body 44, attaching the base member 52 to the intervertebral graft body 44. The base member 52 may have the form of a thin disc, and a corresponding receptacle 58 is provided in the form of a recessed opening defined in the inner side of the fixation plate. The receptacle may have a depth 60 equal to the thickness 62 of the base member 52, for example slightly less than half the thickness of the vertebral fixation plate 26, so that the base member 52 will fit in and mate with the interior of the receptacle, as will now be explained.

Figure 5:
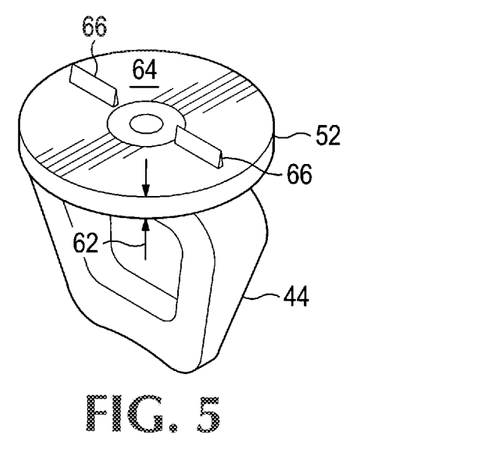
FIG. 5 is an isometric view, from a ventral and caudal viewpoint, showing an intervertebral graft body to which is attached a base member portion of a vertebral fixation plate system as disclosed herein.

An outer face 64 of the base member 52 may be provided with locators 66 in the form of small raised ridges as shown in FIG. 5. The recessed interior or ceiling face 68 of the receptacle 58, defined in the inner side 59 of the fixation plate to receive the base member 52 may be provided with corresponding locator cavities 70 such as grooves. The grooves can receive the locators 66 to keep the vertebral fixation plate 26 stationary with respect to the base member 52 until the vertebral fixation plate 26 has been fastened to the vertebrae by installation of the screws 36.

Figure 6:
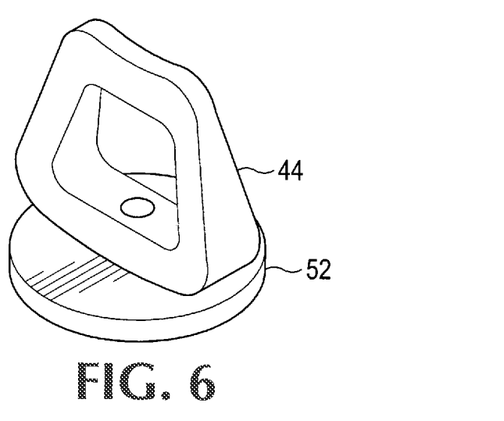
FIG. 6 is an isometric view of the intervertebral graft body and base member portion shown in FIG. 5, taken from the opposite direction.

As may be seen from an opposite viewpoint in FIG. 6, the base member 52 is attached to the graft body 44, and is large enough to extend above and below the intervertebral space 42 where the graft body 44 would be installed between a pair of vertebrae 20, 22.

Figure 7:
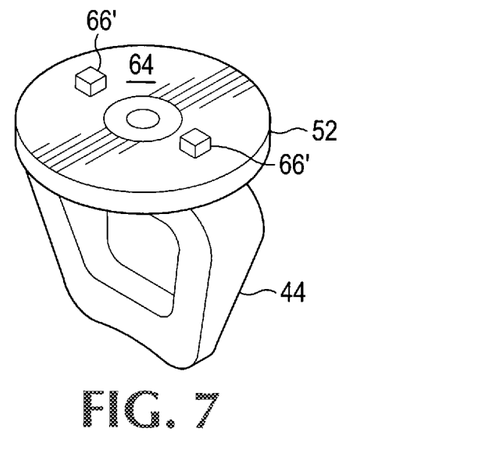
FIGS. 7-10 are isometric views, taken in a direction similar to that of FIG. 5, showing intervertebral graft bodies to which are attached base member portions of the vertebral fixation plate system disclosed herein and which are provided with respective different types of raised locator elements.
Figure 8:
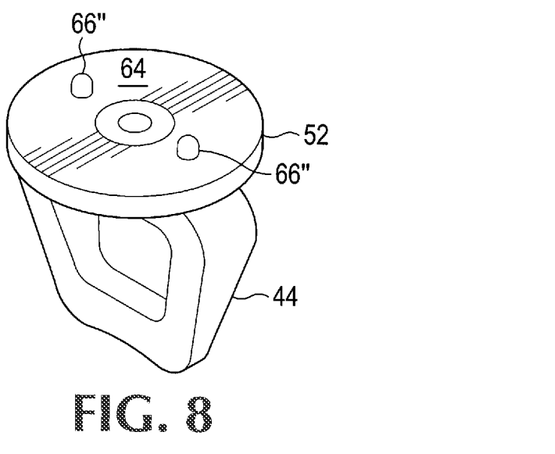
Figure 9:
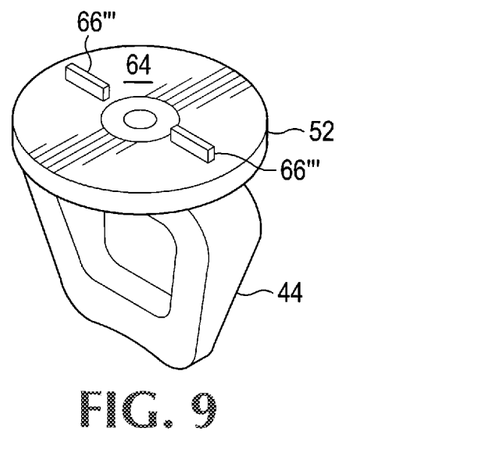
Figure 10:
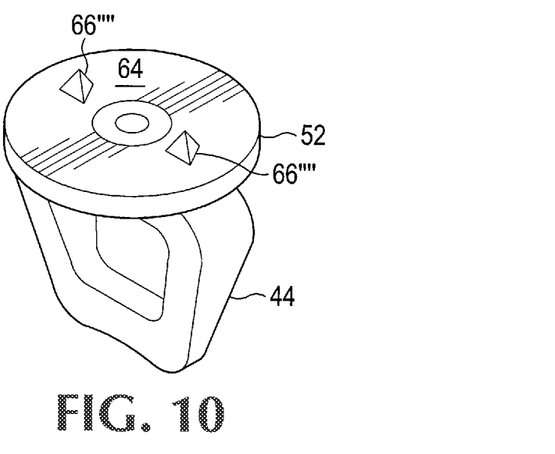

While the outer face 64 of the base member, as shown in FIG. 5, is provided with the small raised ridges as locators 66, locators could be in any of several other forms, as well, such as the small cube-shaped locators 66' shown in FIG. 7, upwardly extending round-ended projections 66" as shown in FIG. 8, small radially-extending rectangular bars 66''', as shown in FIG. 9, or small pyramids 66'''' as shown in FIG. 10. Instead of the base members 52 attached to a graft body 44 by a fastener, such as those shown in FIGS. 5-10, a base member 52 may be provided as an integral part of an interbody fusion device such as that shown in FIGS. 16 and 17.

A group of small locating cavities 70 with shapes and sizes corresponding to those of the locators 66, 66', etc. on a base member 52 are provided, closely spaced in the bottom, or ceiling, surface 68 of the recessed receptacle 58 in the inner side 59 of a mating vertebral fixation plate. The locating cavities 70 can receive the locators 66 with the vertebral fixation plate 26 in any of several slightly different available positions relative to the base member 52 with the base member 52 seated in the receptacle 58 in the inner side 59 of the vertebral fixation plate 26.

Figure 11:
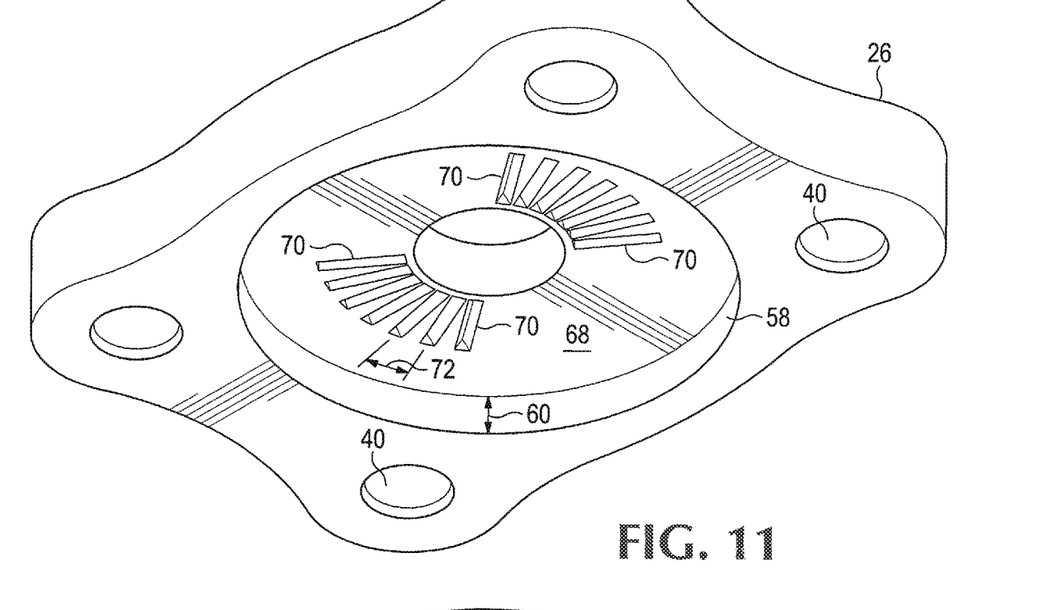
FIG. 11 is an isometric view showing the inner side of a vertebral fixation plate similar to that shown in FIGS. 1 and 2, and also showing a mating base member portion of the fixation plate system, similar to the base member portion shown in FIG. 5, facing toward a recessed receptacle defined in the inner face of the vertebral fixation plate.
Figure 12:
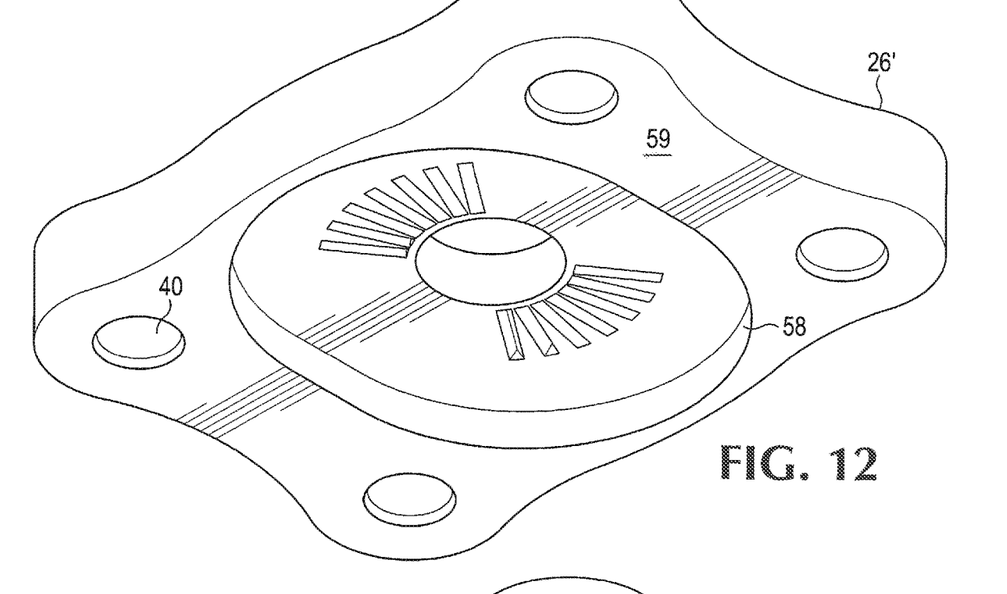
FIG. 12 is an isometric view showing the inner side of a vertebral fixation plate similar to that shown in FIG. 11, but with differently located receptacles for locator elements of a base member portion.
Figure 13:
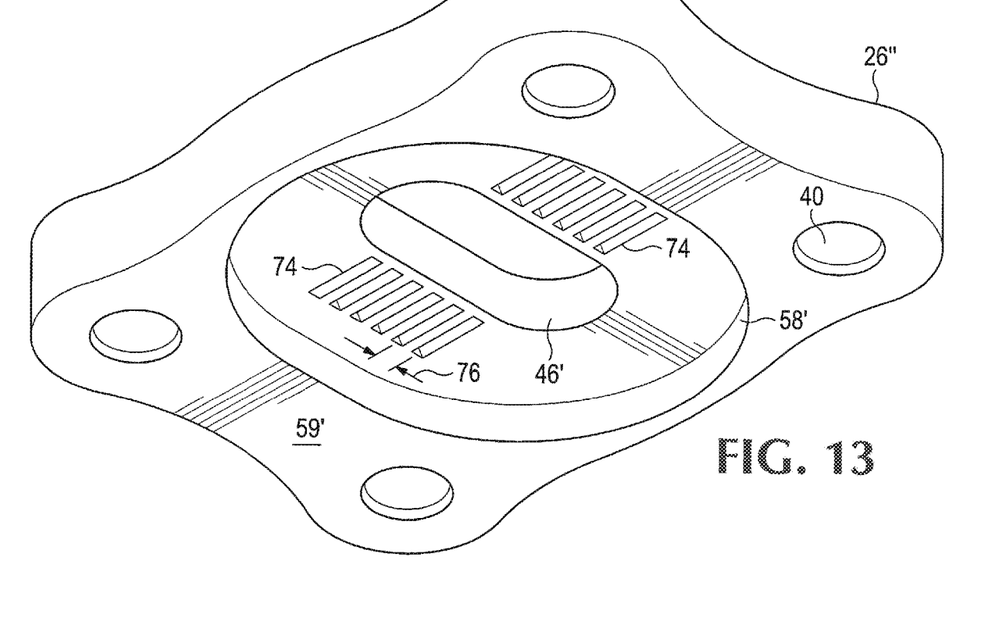
FIG. 13 is an isometric view showing the inner side of a vertebral fixation plate including receptacle grooves arranged parallel with one another and in which the plate includes an elongated central opening.
Figure 14:
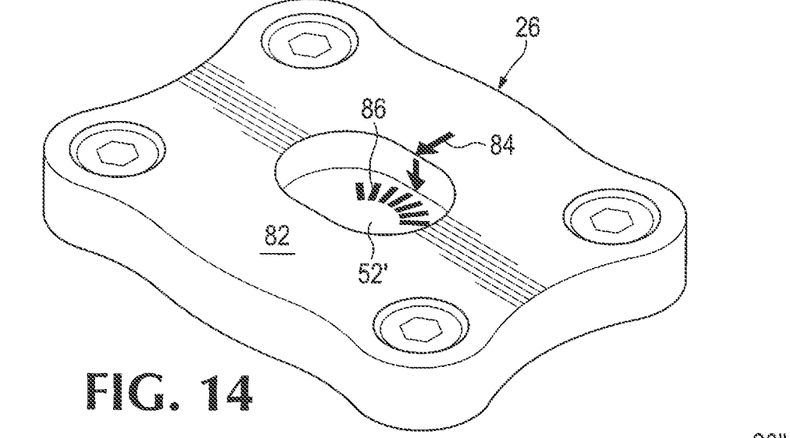
FIG. 14 is an isometric view showing the outer side of a vertebral fixation plate similar to that shown in FIG. 12, and on which there are indicia to show the position of the fixation plate relative to a base member portion of the plate system.
Figure 15:
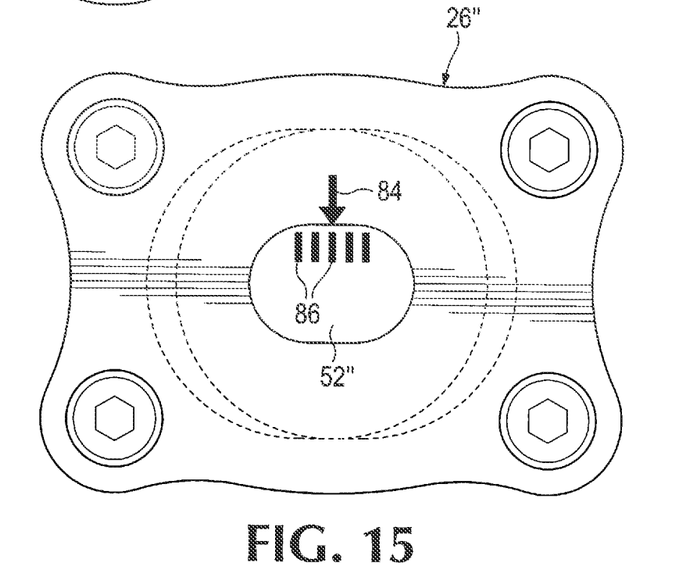
FIG. 15 is a plan view of a portion of a vertebral fixation plate assembly incorporating indicia on a vertebral fixation plate such as that shown in FIG. 14 and on the base member assembled with the vertebral fixation plate, for use in determining the position of the fixation plate relative to the base member.

For example, as shown in FIGS. 11 and 12, locating cavities 70 in the form of grooves may extend radially away from the central opening in the vertebral fixation plate 26 and the location of the screw in the base plate member. The grooves may be spaced apart from each other by small angles 72, such as being separated from one another by intervals of, for example, 5° of rotation of the vertebral fixation plate 26 or 26' with respect to the base member 52, although smaller angular intervals might be used. In another version of the vertebral fixation plate 26'', the central opening in the vertebral fixation plate may be an elongated hole 46', and grooves or other locating cavities 74 may be parallel with each other and spaced apart from one another by a small distance 76, such as 2 mm, to permit the location of the vertebral fixation plate 26'' to be adjusted by translation with respect to the location of the base member 52. In that case, the recessed receptacle 58' defined by the inner side 59' of the vertebral fixation plate will be somewhat larger than the base member 52 leaving room for movement of the base member 52 relative to the interior of the receptacle 58', as shown in FIG. 3 and FIG. 13.

Figure 16:
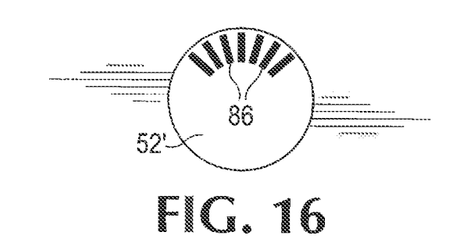
FIG. 16 is a plan view of a base member that may be included in the combination shown in FIG.
Figure 17:
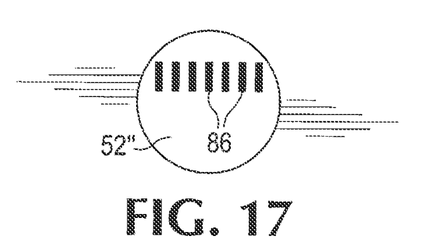
FIG. 17 is a plan view of a different base member useful as a part of a combination such as that shown in FIG. 15.

Referring now to FIGS. 14-17, in one embodiment of the vertebral fixation plate 26 the outer face 82 may include an arrow 84 or other indicia, and the base member 52' may also include indicia such as an engraved or otherwise visible mark 86 for each small angular interval of potential adjustment from a centrally aligned position of mating of the base member 52' with the corresponding vertebral fixation plate 26, as shown in FIG. 16. As shown in FIG. 17, the base member 52'' may also include an engraved or other mark 86 for each small interval step of translation with respect to a corresponding vertebral fixation plate 26'' providing for translation with respect to the base member as shown in the vertebral fixation plate 26'' shown in FIG. 13.

Figure 18:
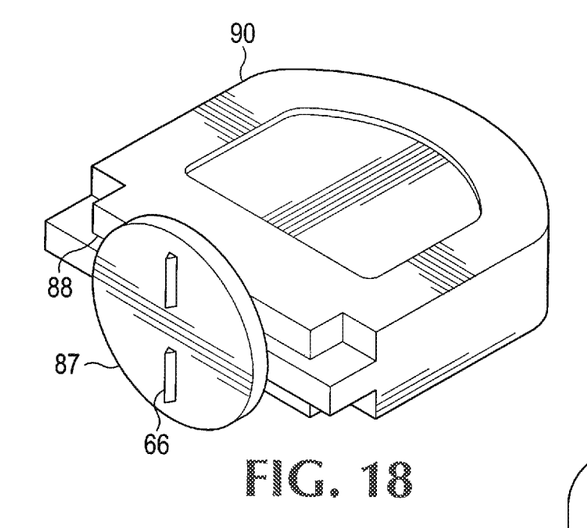
FIG. 18 is an isometric view of an interbody fusion device incorporating a base member for use as part of a vertebral fixation plate assembly according to the present disclosure.
Figure 19:
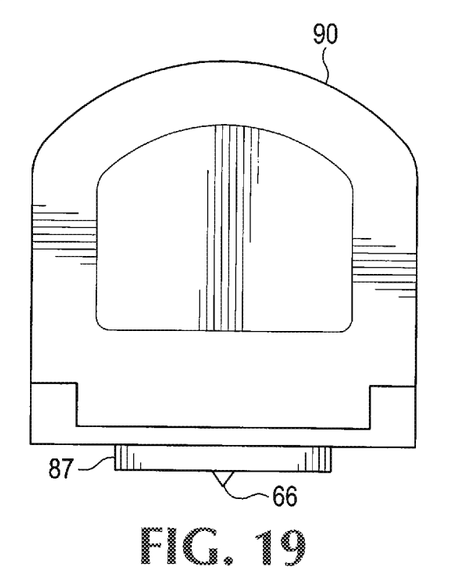
FIG. 19 is a plan view of the interbody fusion device shown in FIG. 18.
Figure 20:
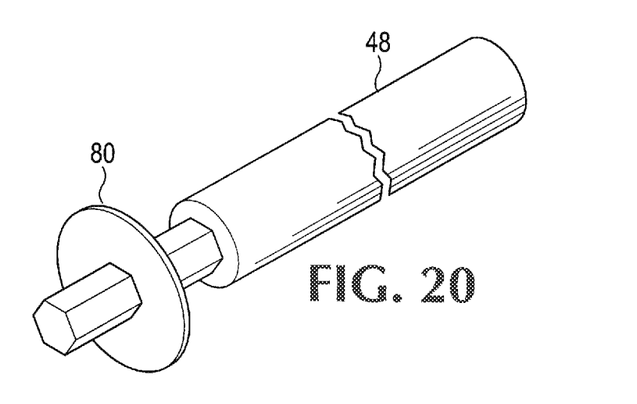
FIG. 20 is an isometric view of a tool for use in installation of a vertebral fixation plate together with a base member incorporated in or attached to an interbody fusion device.

While a suitable base member 52, made to mate with a particular vertebral fixation plate 26 or 26', etc., may be fastened to a conventional interbody fusion device or graft body 44, as shown in FIGS. 3-10, the base member may be integrated with an interbody fusion device or graft body 90, as shown in FIGS. 18 and 19. That is, a base member 87 may be a separate part made to fit into an appropriate slot 88 or other receptacle formed in a related graft body 90, which may be of a particular material intended to encourage and enhance fusion of the adjacent vertebrae 20, 22 after implantation. The base member 87 otherwise may be of a configuration similar to a base member 52 shown attached to a graft body in each of FIGS. 1-10, with one or more locators 66.

In order to quickly establish an optimum location for the vertebral fixation plate of the fixation plate system disclosed herein, a surgeon will make an incision leading to the patient's spine and will retract intervening tissue to gain access to the spine at the level where a disc is to be removed and the adjacent vertebrae are to be fused. The defective disc is removed and a graft body 44 is installed in its place. If the graft body is a conventional interbody fusion device as shown in FIGS. 3 and 4, a base member 52 is fastened to it by a fastener such as the screw 50, so that the result is as shown in FIGS. 1-10.

With the base member 52 exposed and overlapping, or at least not hidden between the adjacent vertebrae 20, 22, the vertebral fixation plate 26 is placed atop the base member 52 or 87, so that the base member 52 or 87 extends into the recessed receptacle 58 in the inner side 59 of the vertebral fixation plate 26. The surgeon estimates the correct position for the vertebral fixation plate 26 and places the fixation plate against the vertebrae 20, 22 so that the base member 52 or 87 is received in the receptacle 58. Optionally, the surgeon may use a tool such as the tool 48 shown in FIG. 1, which may include a flange 80 that can be used to push against the outer face 82 of the vertebral fixation plate 26. Enough pressure is applied to cause the locator or locators 66 on the base member 52 or 87 to enter the closest available locating cavity 70 in the bottom or ceiling face 68 of the recessed receptacle 58, thus establishing an initial position for the vertebral fixation plate 26.

A radiographic image can then be obtained to determine whether the vertebral fixation plate 26 is in the desired location with respect to the vertebrae 20, 22 to which it is to be fastened. If an image suggests that a revised position is necessary, adjustment can be made in defined small steps in the desired direction, either angularly or in translation, depending upon the version of the fixation plate 26 and corresponding base member 52 being used. With marks 86 provided on the outer face 64 of the base member 87 and an arrow 84 on the outer face 82 of the vertebral fixation plate 26, as shown in FIGS. 16 and 17, the initial position of the fixation plate 26 relative to the base member 52 can be noted. The number of defined steps or intervals of movement needed can be determined from the image of the initial position, and the vertebral fixation plate 26 can be moved that distance to place the vertebral fixation plate 26 in an optimum position with respect to the base member 52, where the locators 66 will be received in the closest locator cavities 70 or 74, and the vertebral fixation plate 26 will be located optimally with respect to the vertebrae 20, 22 being fused.

The vertebral fixation plate 26 can then be held in that position, mated against the base member 52, by simple pressure, either using the tool 48 or by manual pressure exerted by the surgeon while the screws 36 are inserted into the receptacles 38 and through the associated holes 40 to fasten the vertebral fixation plate 26 to the vertebrae 20, 22 in a minimum amount of time. It may be most efficient to place a screw 36 into the vertebrae at each of a pair of diagonally opposite corners of the fixation plate 26 initially.

The definite retention of the vertebral fixation plate 26 in the chosen position, as a result of the mating of the locators 66 in the locator cavities 70 within the receptacle 58 defined in the inner side 59 of the vertebral fixation plate 26, gives the assurance that the vertebral fixation plate 26 will be located properly with respect to the space 42 between the vertebrae 20, 22 and as to alignment with the portion of the spine where vertebral fusion is to take place.

While the vertebral fixation plate system 24 disclosed above has addressed a single-level spinal fusion procedure, the system can similarly be used for fusion at one or more adjacent additional levels by utilizing a similar but longer vertebral fixation plate, long enough to extend to where it can be fastened to each of the involved vertebrae and including a recessed receptacle 58 to be mated with a base member 52 attached to a graft body 44 or incorporated in a graft body 90 implanted in the intervertebral space 42 at one of the levels where fusion is to take place.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A vertebral fixation plate system, comprising:
   (a) an interbody fusion graft body having a front face;
   (b) a vertebral fixation plate having an inner face, and an outer face and defining a plurality of primary fixation fastener receptacles each located in a respective position to receive a respective fastener extending therethrough into one of a pair of adjacent vertebrae to be held in a fixed positional relationship to each other;
   (c) a base member attached to the front face of the graft body, the base member having a thickness and an outer face;
   (d) a base member receptacle defined in the inner face of the vertebral fixation plate, the base member receptacle having a ceiling and a depth in a direction corresponding to the thickness of the base member and having dimensions, in respective directions generally parallel with plane of the vertebral fixation plate, at least great enough so that the base member receptacle can receive and contain the base member and the base member can be repositioned with respect to the vertebral fixation plate by at least one of rotation or translation while remaining in the base member receptacle;
   (e) an opening defined and extending through the vertebral fixation plate from the outer face thereof into the base member receptacle and located so as to expose a portion of the outer face of the base member to view, through the opening, when the base member is located within the base member receptacle; and
   (f) respective mating parts located respectively on the outer face of the base member and on the ceiling of the base member receptacle, the mating parts including a raised locator body on one of the outer face of the base member and the ceiling of the face member receptacle, and a plurality of corresponding locator cavities defined in the other one of the outer face of the base member and the ceiling of the face member receptacle, the mating parts being capable of mating with each other with the vertebral fixation plate in each of a plurality of defined positions with respect to the base member, so that the mating parts resist movement of the vertebral fixation plate relative to the base member.

2. The vertebral plate fixation system of claim 1 wherein the vertebral fixation plate has a thickness and the outer face of the base member is flat, except for the mating part, and wherein the base member has a thickness about half that of the vertebral fixation plate.

3. The vertebral plate fixation system of claim 1 wherein the depth of the base member receptacle in the vertebral fixation plate is equal to the thickness of the base member.

4. The vertebral fixation plate system of claim 1, wherein the plurality of the locator cavities are located in the ceiling.

5. The vertebral fixation plate system of claim 1 wherein the raised locator body is a raised ridge and the corresponding locator cavities are grooves.

6. The vertebral fixation plate system of claim 5 wherein a plurality of the grooves are located alongside each other and parallel with each other.

7. The vertebral fixation plate system of claim 5 wherein a plurality of the grooves are located alongside one another and spaced apart from one another by an angular interval between consecutive ones of the grooves.

8. The vertebral fixation plate system of claim 1 wherein the raised locator body is in the form of a cube.

9. The vertebral fixation plate system of claim 1 wherein the raised locator body is in the form of a rectangular bar.

10. The vertebral fixation plate system of claim 1 wherein the raised locator body is in the form of an upwardly extending round-ended projection from the outer face of the base member.

11. The vertebral fixation plate system of claim 1 including first indicia on the outer face of the vertebral fixation plate and second indicia on the portion of the outer face of the base member exposed to view through the opening in the vertebral fixation plate.

* * * * *

UNITED STATES PATENT AND TRADEMARK OFFICE
CERTIFICATE OF CORRECTION

| | |
|---|---|
| PATENT NO. | : 10,610,372 B2 |
| APPLICATION NO. | : 15/093494 |
| DATED | : April 7, 2020 |
| INVENTOR(S) | : Robert L. Tatsumi |

It is certified that error appears in the above-identified patent and that said Letters Patent is hereby corrected as shown below:

In the Specification

Column 4, Line 30: Please change "included in the combination shown in FIG." to read --included in the combination shown in FIG. 15.--

Column 7, Line 39: Please change "70 or 74, and the vertebral fixation plate" to read --70, and the vertebral fixation plate--

Signed and Sealed this
Sixth Day of December, 2022

Katherine Kelly Vidal
*Director of the United States Patent and Trademark Office*